United States Patent [19]
Faulhaber et al.

[11] 3,958,127
[45] May 18, 1976

[54] OPTICAL-ELECTRICAL WEB INSPECTION SYSTEM

[75] Inventors: Mark E. Faulhaber; Edmund H. Smith, Jr., both of Wilmington, Del.

[73] Assignee: E. I. Du Pont de Nemours and Company, Wilmington, Del.

[22] Filed: Aug. 9, 1974

[21] Appl. No.: 496,319

[52] U.S. Cl. .............................. 250/563; 250/572; 250/227; 356/239
[51] Int. Cl.² .............................................. G01N 21/32
[58] Field of Search ........................ 250/560–563, 250/571, 572, 236, 227, 214 R; 356/168, 159, 160, 200, 237, 239

[56] References Cited
UNITED STATES PATENTS

| | | | |
|---|---|---|---|
| 3,001,080 | 9/1961 | Neil | 250/562 |
| 3,061,731 | 10/1962 | Thier et al. | 356/200 X |
| 3,427,462 | 2/1969 | Cist | 250/562 |
| 3,493,769 | 2/1970 | Revesz et al. | 250/214 R |
| 3,556,664 | 1/1971 | Blaisdell et al. | 356/200 |
| 3,646,353 | 2/1972 | Bhullar et al. | 356/200 X |
| 3,728,548 | 4/1973 | Pinior | 250/227 X |
| 3,744,905 | 7/1973 | Smith | 356/168 X |
| 3,843,890 | 10/1974 | Anthony, Jr. et al. | 250/572 X |

Primary Examiner—Walter Stolwein

[57] ABSTRACT

An automatically calibrated flying spot web inspection system adapted to detect transverse (or roll mark) defects and discriminate these defects from other defect types. Electronic circuit means responsive to a beam of radiation in either the reflection mode or the transmission mode detect and discriminate these defects from the other types.

2 Claims, 7 Drawing Figures

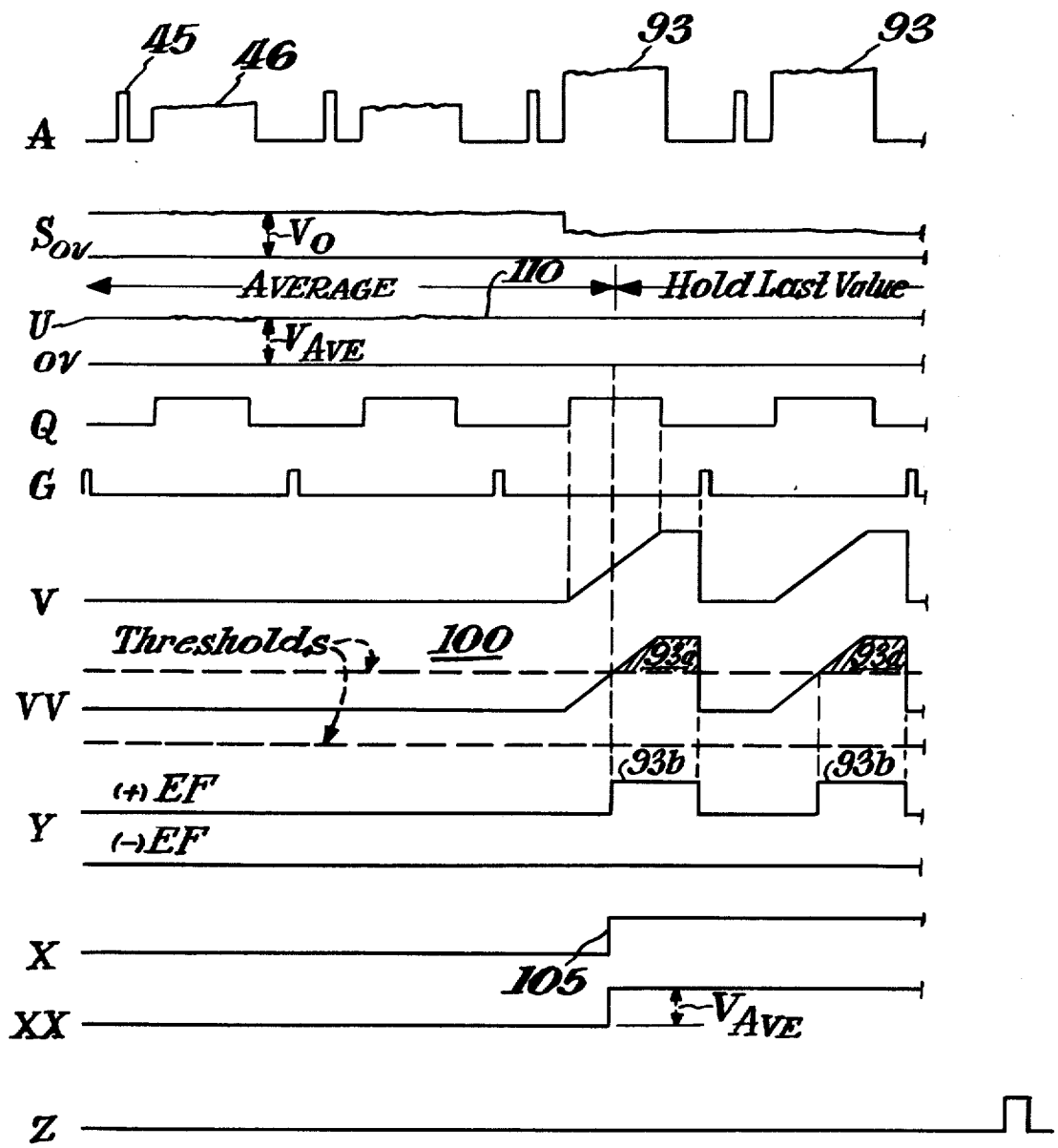

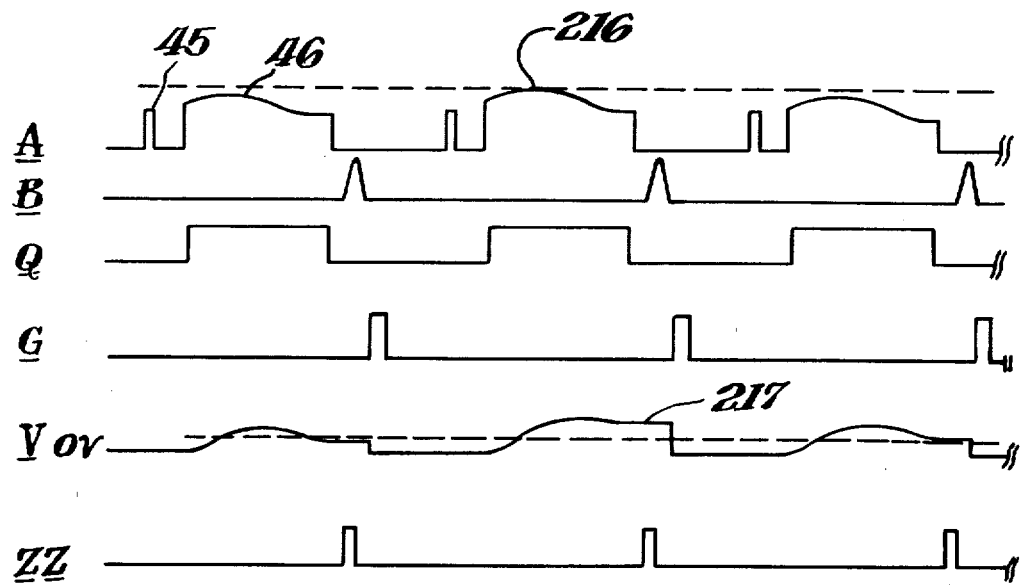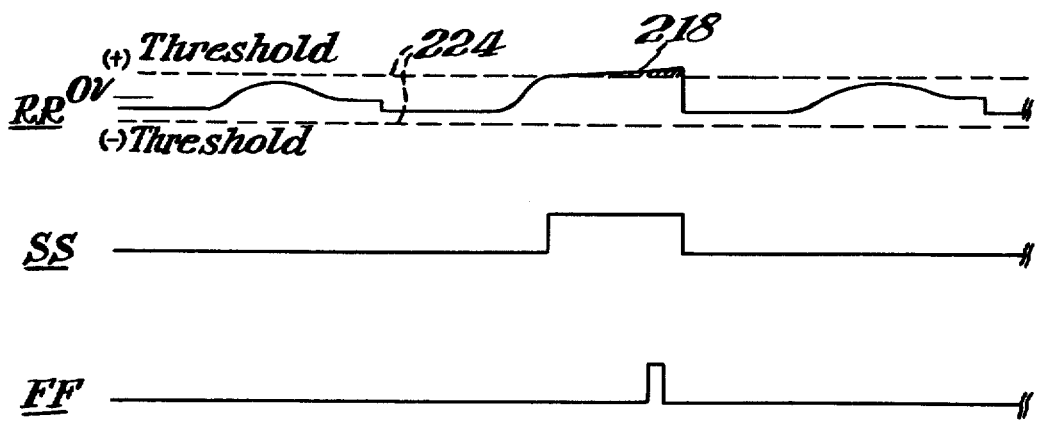
Fig. 54.

OPTICAL-ELECTRICAL WEB INSPECTION SYSTEM

BRIEF SUMMARY OF THE INVENTION

Generally, this invention relates to a flying spot inspection system for web materials comprising a radiation source, means traversing a beam of radiation from the source in a scan across the web, electronic means responsive to the beam of radiation in either the reflection mode or the transmission mode with respect to the web detecting the existence of transverse defects, such as "roll mark" defects, having narrow width (in the direction of web advance) and substantial length (in a direction generally transverse the web) and discriminating said defects as a class. For maximum benefits, it is preferred to utilize the roll mark defect detector of this invention in conjunction with the flying spot inspection system of Application Ser. No. 383,289, filed July 27, 1973, now U.S. Pat. No. 3,843,890, which detects and discriminates defects of the three general classes: (1) sharp edge defects, (2) diffuse edge defects and (3) protracted duration defects characterized by an amplitude-shifted pedestal of the optical-to-electrical transduction signal produced in the scan of the web, in which case common use can be made of the optical scanner and the automatic calibration means for the system as a whole.

CROSS REFERENCE TO RELATED APPLICATION

This application is directed to an optical-electrical web inspection system which can optionally be merged with the optical-electrical web inspection system which is the subject matter of Application Ser. No. 383,289 filed July 27, 1973.

DRAWINGS

The following drawings constitute part of this specification, in which.

Figure 3:
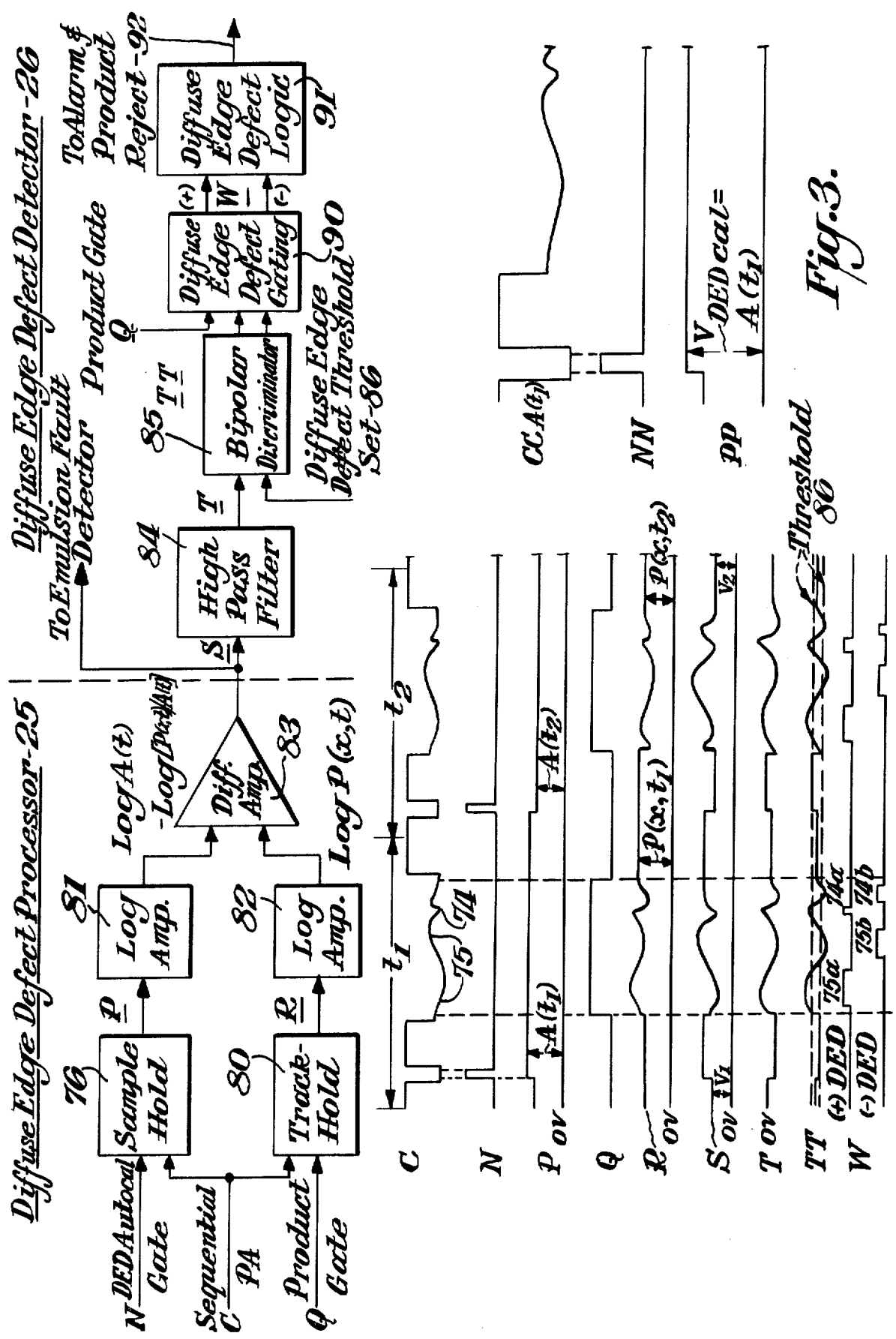
Figure 4:
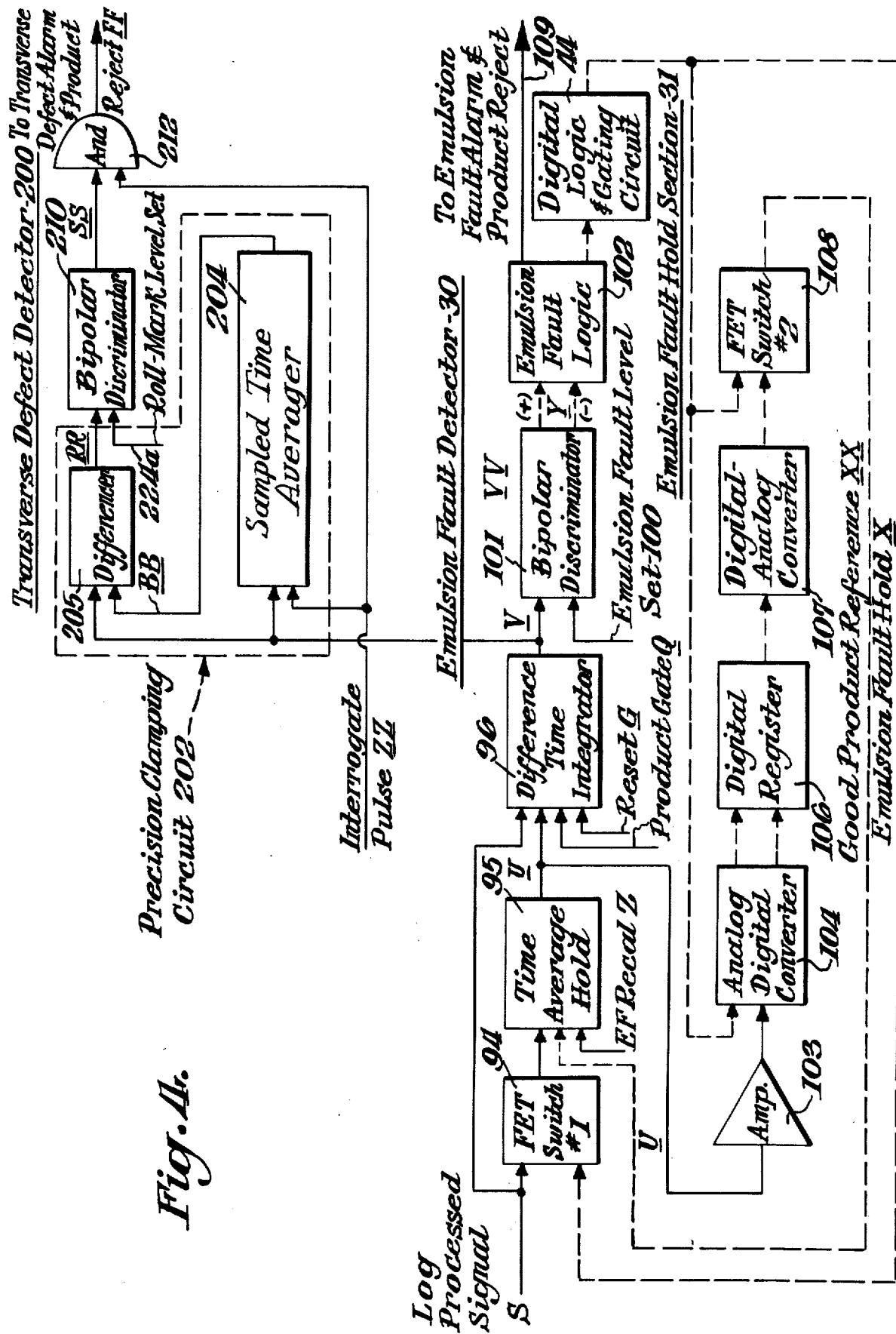
Figure 5:
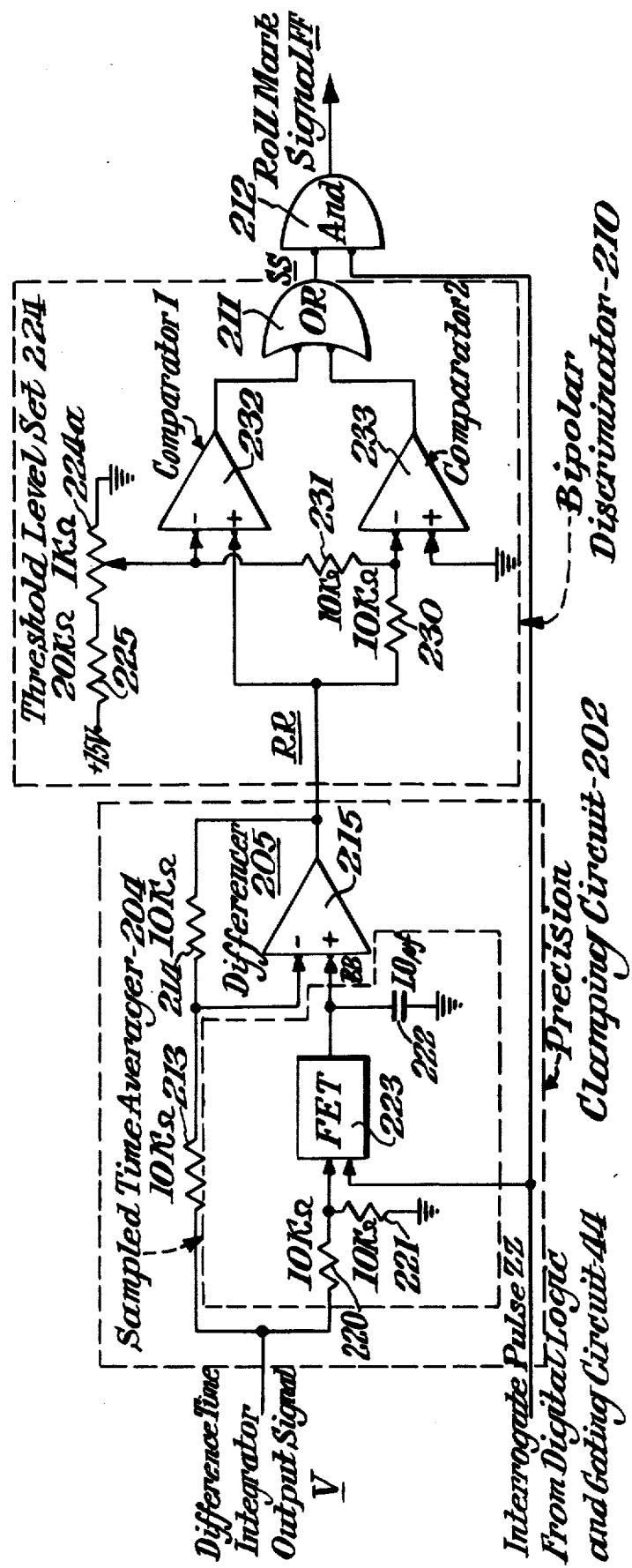

FIG. 3 is a block diagram of a diffuse edge defect (DED) detector and processor together with associated electrical signal waveforms, FIG. 4 is a block diagram of a protracted duration defect (DED) detector corresponding with an emulsion fault (EF) or splice in the X-ray film example, with hold auxiliary, showing also in block addition the improvement of this invention, FIG. 4A is a diagrammatic representation of some of the electrical signal waveforms existing in particular parts of the circuitry of FIG. 4, FIG. 5 is a detailed schematic diagram of the circuit of this invention, and FIG. 5A is a diagrammatic representation of electrical signal waveforms existing in particular parts of the circuitry denoted in FIG. 5.

BACKGROUND

The manufacture of high-quality continuous web products, such as X-ray film unprinted fabrics, metal foils and the like requires highly reliable inspection and, preferably, discrimination of defects as to their nature.

This invention constitutes an improved flying spot web scanning system which can be used in either the radiation transmission or reflection mode to examine transparent or translucent webs, such as photographic film or polymeric wrapping materials, or light-opaque material such as aluminum foil, textile webs or the like where radiation transmission is capable of indicating holes or occlusions in the web, whereas radiation reflection indicates surface defects or conditions.

For purposes of this description, X-ray photographic film web is taken as the detailed example, because it must be fabricated to extremely high quality standards and the inspection preferably employed is in both the radiation transmission and reflection modes.

Application Ser. No. 383,289, hereinabove mentioned, has proved effective in detecting and discriminating three general classes of defects in X-ray photographic film, which classes are, however, encountered in various counterparts in many other web products besides film, i.e., (1) sharp edge defects, which are most often small in size, including for X-ray film: gel pox, base carbon, pinholes, coated dirt and the like, and, for textile webs: holes, jet tracks and fiber clumps, (2) diffuse edge defects, which are most often larger in size than sharp edge defects but have less distinct edges, including, for X-ray film: drying streaks and disturbed coatings and, for textile webs: large clumps and changes in basis weight and (3) protracted duration defects which, typically, consist of full web width anomalies, such as splices, large area absences of coating, changes in web gage and the like.

The invention of this Application is intended to detect, and discriminate, a class of defects which is arbitrarily denoted "transverse defects," which generally consist of subtle non-uniformities which run laterally across either part of or the entire width of the product and, typically, have widths (measured in the "machine," or product advance direction) of from hairline thickness to about 0.25 to 4 inches. In X-ray film product such defects can be produced by a localized thinning, or thickening, of the photographic emulsion whenever the production line stops and the freshly coated film comes near to, or into contact with, the process rolls, giving rise to the terms "roll mark" and "stick mark" in designation of these defects. Entirely apart from X-ray film manufacture, these defects usually result from chatter or vibration in bar type coaters which, in normal operation, deposit material evenly on substrates moved transverse thereof. Transverse defects, as intended herein, are thus encountered in the tin coating of steel strip, and also evidence themselves as transverse waves appearing in plate glass during its manufacture.

Moreover, an accentric roll in a process line may apply tension, or compression, to a running strip product, creating relatively thin, or thick, local transverse regions. In the paper industry, undesired water marks formed by intermittent roll contact with wet paper pulp as laid down on the Fourdrinier wire, or embossing effected by eccentric rolls, exist as other transverse type defects.

Transverse defects were detectible as protracted duration defects of class (3) supra, but emulsion fault circuit sensitivity was limited, primarily due to signal pedestal non-flatness. Such non-flatness causes the integral value of the instantaneously tested pedestal minus the average value of many pedestals to be non-zero. It has been found that this pedestal non-flatness for normal product can produce a signal resembling that of a roll mark defect, thereby giving a false reject classification of product which is perfectly acceptable in the market place. Accordingly, there was need for a detector reserved exclusively to transverse defects having improved discrimination capability, which constitutes the subject matter of this invention. Moreover, it was advantageous to effectively engraft the roll mark detector on the inspection system of said Application Ser. No. 383,289 without any disturbance to operation of the latter and, ideally, with full mutual compatibility therebetween.

THE INVENTION

Accordingly, this invention comprises a circuit designed to (1) sample the emulsion fault difference time integral at the end of each scan (instead of throughout the full scan), but before integrator reset, (2) provide uniform sensitivity to roll mark defects in the presence of a long term offset input and (3) provide an adaptable reference for comparison having a shorter time constant than the time average reference in the emulsion fault circuit, but a longer time constant than that which would be evidenced by a roll-mark type defect. The system can function independently of, but is most economically embodied in, an auxiliary circuit to the apparatus of Application Ser. No. 383,289. When this is done, the auxiliary circuit of this invention is adapted to discriminate at much lower signal threshold levels in the detection of such subtle defects as "roll-mark" defects.

Basically, the method of this invention comprises integrating the difference signal between the instantaneous calibrated gated pedestal signal and its time-averaged value over many scans, sampling the held integral value at the end of each scan, obtaining a short-term time average of these sampled integral values, comparing the sampled value short-term time average with the instantaneous integral value, discriminating the differences using a bipolar discriminator having preselected (+) and (−) thresholds and giving an alarm for each signal exceeding the preselected threshold values at the sampling instant.

Since the apparatus of this invention utilizes the optical and electrical transducing equipment in common with that of said Application Ser. No. 383,289, reference is made to the description of the latter Application for most complete details of circuit construction and operation, only enough of the latter being repeated here to provide an understanding of the basic design without excessive repetition.

In summary, the apparatus of Application Ser. No. 383,289, with which the present invention is preferably combined, comprises an analog/digital inspection system which includes means recalibrating automatically, scan-by-scan, sharp edge, diffuse edge and protracted duration and, by this invention, roll (or stick) mark fault detection circuits. These circuits receive informational signals from a single photodetector assembly (one for each inspection channel); however, calibration and defect detection and identification are accomplished by using two corresponding yet distinct forms of the same calibration signal such that each eliminates the adverse effects of both short- and long-term system parameter fluctuations in evaluating a particular class of defect.

Since roll mark defects can be sensed by any of the three inspection channels of the system of said Application Ser. No. 383,289, only the transmission mode channel of said Application is described in detail herein.

Referring to FIGS. 1, 2, 3 and 4 particularly the flying spot scanner, denoted generally at 20, utilizes a laser source (not detailed) directed at a multifaceted rotating mirror reflector (not shown) which, with associated beamforming optics (not detailed) produces a highly collimated scanning radiation beam. This beam sweeps a spot of radiation 21 transversely across the running product web 22 at a high enough velocity to ensure that successive scans overlap sufficiently to complete product inspection.

During each scan, the beam passes over a radiation attenuation filter, the assembly of which is denoted generally at 23, FIG. 1, which comprises the automatic calibration means, referred to hereinafter as the "AUTOCAL filter," immediately prior to the web scan. This produces the calibration signal which is routed to the analog shapr edge defect detector 24 and the diffuse edge defect processor 25. The emulsion fault detector 30 (which latter is the X-ray film inspection system counterpart of the protracted duration defect class detector of the general description) is calibrated indirectly with reference to the AUTOCAL calibration signal, all as described in said Application Ser. No. 383,289.

A radiation-conducting rod collector 32 (not detailed) conveys the energy from the beam which is transmitted through an AUTOCAL filter (not shown), plus that which is reflected from, or transmitted through, the running product web 22, to a photomultiplier (PM) receiver 33. Referring to FIGS. 4A and 5A a time sequential electrical signal A is thereby generated for each scan, in which there appears in sequence from left to right an AUTOCAL pulse 45 followed by a product pedestal signal 46. The AUOTCAL component 45 of this signal is used in the circuitry to establish basic reference voltage signals and sensitivity levels in the several defect detection circuits for analysis of the succeeding product pedestal portion of each scan waveform.

Details of a three-channel inspection system and the complete optical arrangment utilized therein are set forth in said Application Ser. No. 383,289, to which reference is again made, and are, therefore, not repeated here.

Figure 1:
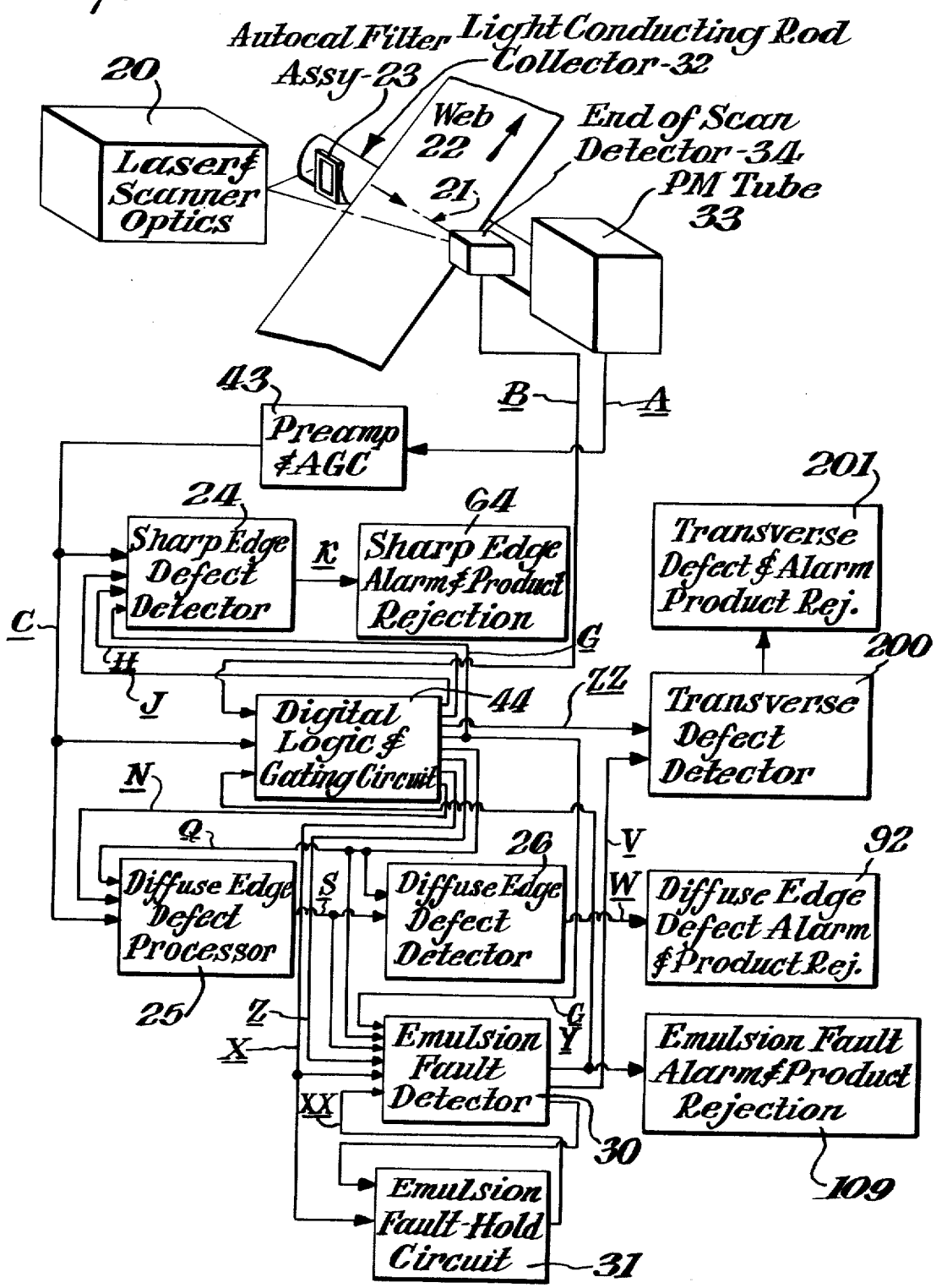
FIG. 1 is a block diagram of the entire inspection system.

As shown in FIG. 1, a suitable preamplifier and automatic gain control stage 43 is interposed between PM tube 33 and the defect detection circuits. This stage boosts the signal amplitude and isolates photomultiplier 33 from possible loading effects of the succeeding inspector stages, whereas the automatic gain control ensures that the output signal amplitude remains within preselected limits in order that changes in laser intensity or PM tube efficiency do not degrade the system performance.

Figure 2:
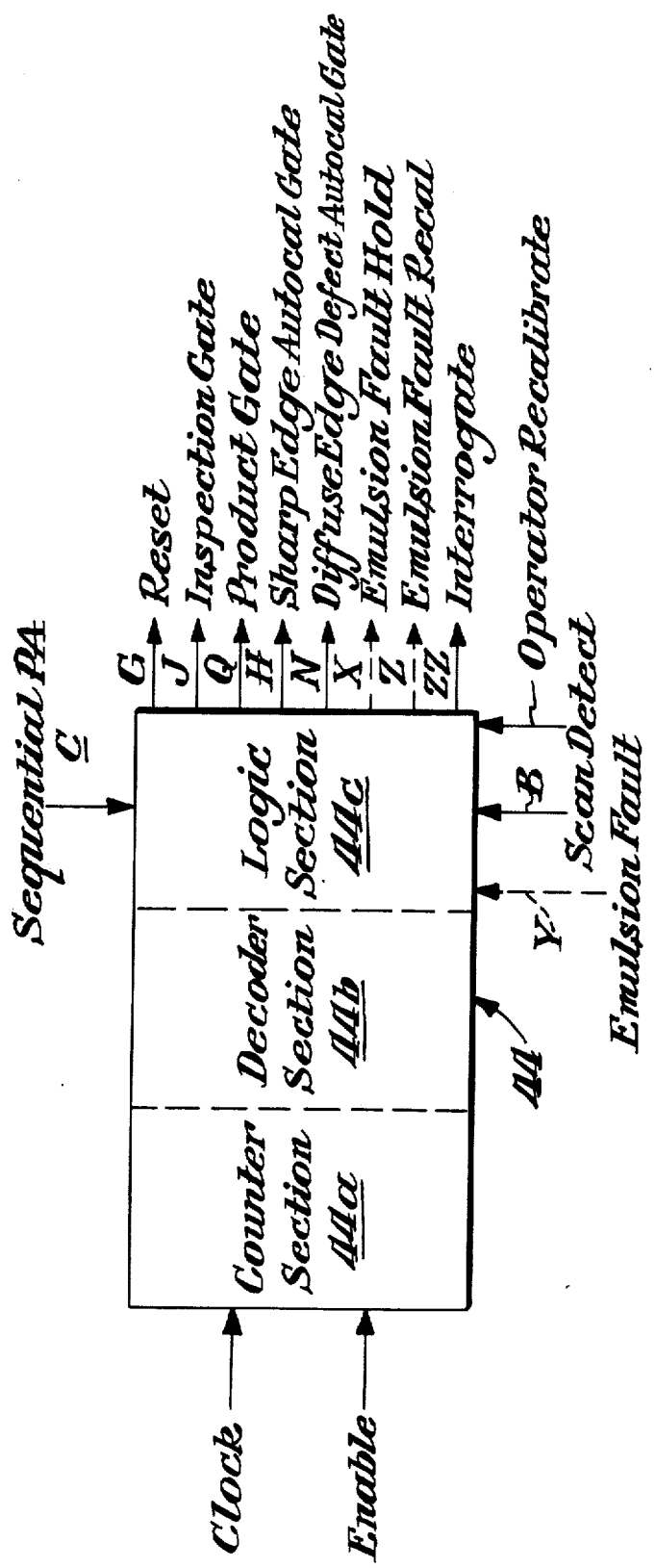
FIG. 2 is a block diagram of the Digital Logic and Gating Section arrangement.

Referring to FIGS. 1 and 2, digital logic and gating circuit 44 incorporates a counter section 44a, a decoder section 44b and a logic section 44c, and generates all of the timing gates for the analog section hereinafter described. In addition, a circuit (not shown) within circuit assembly 44 conditions the defect signals so that a computer can be thereby controlled to activate alarms, initiate the marking, slitting and chopping operations necessary to separate defective product from acceptable product at a convenient point in the finishing process, and to perform a data analysis on the defects detected.

FIG. 2 shows the essential inputs to, and outputs from, circuit 44, which are denoted by alphabetic letters which correspond with the waveforms shown in FIGS. 3, 4A and 5A. Thus, the inputs consist of the time sequential preamplifier signal C, emulsion fault Y, scan detect B and high frequency stable clock signals effecting time coordination for the entire inspection system. The scan detect signal B initiates the reset pulse G, whereas the combination of an AUTOCAL pulse 45 leading edge, clock pulses, a counter and appropriate decoders set and reset flip flops to generate the sharp edge defect AUTOCAL gate H, not further described, and the diffuse edge defect AUTOCAL gate N. The inspection gate J, not further described, and the product gate Q and interrogate signal ZZ are formed similarly, except that the product pedestal 46 leading edge is used in place of AUTOCAL signal 45 to initiate formation of these gates. The emulsion fault hold signal X is initiated at the instant that an emulsion fault Y is detected. To recalibrate the emulsion fault circuitry at the beginning of a new product run, the operator manually initiates an emulsion fault recalibrate signal Z. The gates which are formed as described have extremely precise widths, which are required to pass selected portions of the AUTOCAL pulse and pedestal portion of the high repetition rate sequential preamplifier signal C. In this connection, each scan requires that the diffuse edge defect AUTOCAL gate N fall precisely within the bounds of AUTOCAL pulse 45, which may be as narrow as 1–2 $\mu$ sec.

Referring back to FIG. 1, the diffuse edge defect processor 25 receives the sequential preamplified input signal C and uses product gate Q and DED AUTOCAL gate N from the digital logic and gating circuit 44 to produce a calibrated output signal S. As hereinafter described, calibrated signal S is essential not only for the detection of diffuse edge defects, not further described, but also for the detection of the emulsion fault defect class and subtle transverse type defects, exemplified by the roll mark defects described, i.e., the object of this invention.

FIG. 3 shows a preferred embodiment of the diffuse edge defect processor 25 and the characteristic electrical signal waveforms which aid in understanding this circuit's operation.

The sequential preamplified input signal C shows a sharp edge defect 74 superimposed on a larger undulating type product defect 75, which appears over two successive scan periods $t_1$ and $t_2$. The second scan period signal, labeled $t_2$, shows amplitude-reduced AUTOCAL and pedestal components due to a change in incident illumination typically caused, for example, by a difference in the reflectivity of the adjacent facets of the scanner rotating mirror.

The amplitude of the successor AUTOCAL pulse $A(t_1)$, is sampled during the AUTOCAL gate N interval and is then held to produce the diffuse edge defect AUTOCAL reference P. Waveforms CC, NN and PP, corresponding to waveforms C, N and P, respectively, are enlarged views of the diffuse edge defect AUTOCAL signal formation. The AUTOCAL sample-hold circuit 76 maintains this reference, $A(t_1)$, until replaced by the next sample, $A(t_2)$. Simultaneously, a track-hold circuit 80 follows the variations of the product pedestal, $P(x,t_1)$, passed through the action of the product gate Q, and holds the final product value $P(x,t_1)$ until the occurrence of the next product gate signal Q, thereby producing $P(x,t_2)$ shown in waveform R. For the situation illustrated, both the diffuse edge defect AUTOCAL P and product pedestal amplitudes R decrease as a result of the reduction in scan illumination.

Using the conventional technique of differencing the logarithms of two factors to produce the logarithm of their ratio, the diffuse edge defect AUTOCAL P and product pedestal R signals are logarithmically processed by log amplifiers 81 and 82, respectively, and their differences taken by the difference amplifier 83 to produce the logarithmic ratio, $(-) \log [P(x,t)/A(t)]$, represented by signal waveform S.

Since both $P(x,t)$ and $A(t)$ signals are influenced by the same system proportionality factor $K(s,t)$, described in said application Ser. No. 383,289, this factor cancels out when the ratio is taken, and waveform S consequently contains calibrated defect information. Accordingly, defect amplitudes are defined in terms of percentages of the product signal, not product plus noise signal level.

To achieve this result, however, it is necessary to preselect the diffuse edge defect AUTOCAL signal P level by appropriate selection of the AUTOCAL radiation attenuation filter 23 material to provide the appropriate gain that will either more, or less, accentuate the defects as a percentage of the product pedestal signal height. (Waveform S illustrates the case where the defects have been accentuated.)

Any difference between signal levels $V_1$ and $V_2$ in the log-processed ratio signal waveform S during any two successive scan periods indicates the existence of an emulsion fault, splice or subtle transverse (e.g., roll mark) defect condition identified by a change in pedestal level without a corresponding change in the AUTOCAL pulse height. This particular defect class, (the protracted duration defect), will be sensed (but not necessarily identified) by either the emulsion fault or the transverse defect detectors hereinafter described.

FIG. 4, taken together with the applicable signal waveforms depicted in FIG. 4A, shows a preferred embodiment of emulsion fault detector 30 for the discrimination of this type fault.

Referring to FIG. 4A, signal waveform A represents a succession of four scans in a radiation transmission channel in which an emulsion fault 93, in this instance an emulsion miss, or roll mark defect, occurs in the last two scans. This fault is immediately recognizable, since the pedestal height suddenly rises above the AUTOCAL pulse 45 height. (Conversely, a comparatively low pedestal signal would also represent an abnormally heavy emulsion or splice.) However, since the operation of the sharp edge defect detector, not here described, depends upon differentiation of the pedestal signal and the operation of the diffuse edge defect detector, not here described, depends upon high pass filtering a non-pulsating DC signal, neither detector system will discriminate the transverse defect class (such as a roll mark type) which causes a change in pedestal level with respect to the amplitude of AUTOCAL signal 45. To discriminate this class of defect, the emulsion fault detector 30 functions to compare the instant log-processed and calibrated signal S with its time-averaged value U over many scans, such that the resulting time-integrated difference signal V is used to detect a fault. This timeintegrated difference signal V can be used to detect subtle transverse defects which yet remain within the emulsion fault thresholds 100, having values set according to the degree of pedestal non-flatness.

Log processed ratio signal S received from hereinbefore described diffuse edge defect processor 25 has an initial amplitude $V_o$ in the instance here described and passes through a field effect transistor (FET) switch No. 1, 94, normally closed, to a time-average-hold circuit 95. The output U of this circuit is the time-averaged value of S over many web scans, and has an amplitude $V_{AVE}$ approximately equal to $V_o$.

The difference between the amplitudes of the two signals S and U is time-integrated by the difference time integrator circuit 96 during the period that it is activated by product gate Q. At the end of each product scan, reset pulse G switches the integrator circuit 96 to return its output to the base line level, thereby dumping the accumulated value to produce the output waveform V. When signal V exceeds the preset thresholds 100 in waveform VV in the bipolar discriminator 101, as indicated by 93a, a corresponding positive fault signal 93b is output in waveform Y. Negative polarity fault signals produce corresponding negative counterparts in waveform Y and, for both polarities, the durations correspond to the severity of the faults. The emulsion fault logic section 102 receives the emulsion fault signal Y and, in response, produces the appropriate alarm and product rejection effectuation output signal 109, which causes the digital logic and gating circuit 44c to produce an emulsion fault hold signal X.

Signal X effects two results, namely: (1) it opens FET switch No. 1, 94, and (2) it causes the time-average-hold circuit 95 to stop averaging the log processed ratio signal S and substitute in its place a "good product" reference signal XX with amplitude $V_{AVE}$ produced by the emulsion fault hold circuit 31. Several scans after the emulsion fault condition has cleared (typically, two defect-free scans is preselected as the clearance interval), the digital logic and gating circuit 44 will cause the emulsion fault hold signal X to return to its base line value, thereby closing FET switch No. 1, 94, and restoring the operation of the time-average hold circuit 95.

Maintenance of a long-term stability of the "good product" signal amplitude XX is imperative, as this level represents, to the inspector, the best information available within a product run of good product quality. Since short- and long-term variations have already been taken into account, signal XX constitutes an absolute comparison standard for good product transmissivity or reflectivity, as the case may be.

Additionally, the emulsion fault hold signal X activates the emulsion fault hold circuit 31, which operates in the following manner.

The time-averaged signal U received from emulsion fault detector section 30 is amplified by amplifier 103 and is then sampled by the analog-digital converter 104 at the instant the leading edge 105 of the emulsion fault hold step function X passes. This sampled signal amplitude is converted into digital form by analog-digital converter 104, which enables and loads the digital register 106. As long as the emulsion fault hold signal X prevails, digital register 106 will maintain its loaded value invariant, regardless of succeeding signal variations seen at the input of the analog-digital converter 104. A digital-analog converter 107 converts the digital register output signal back to analog form which, after passing through FET switch No. 2, 108, now becomes the "good product" reference signal input XX, $V_{AVE}$, supplied to the emulsion fault detection section 30. Waveform XX shows that, until the occurrence of the emulsion fault hold signal X, the "good product" reference is at ground state, but then jumps to a value $V_{AVE}$ matching the last known time-average signal amplitude 110 unaffected by the detection of an emulsion fault condition 93.

The FET switch No. 2, 108, which closes at the occurrence of the emulsion fault hold signal X, causes the substitution of the "good product" reference XX for the time-averaged log processed ratio signal S in the time-average-hold circuit 95. The output of circuit 95 now becomes the fixed amplitude-level "good product" reference XX with value equal to the time-averaged signal U having amplitude 110 at the exact instant that the emulsion fault hold signal X leading edge 105 passes.

It will be understood that with normal product or optical system spatial variations that contribute to pedestal non-flatness, such as shown in waveform A, FIG. 5A, the difference-time integrator circuit 96 will produce a substantial integrated difference value, waveform V. Consequently, the emulsion fault level 100 would then have to be set at a sufficiently high level to prevent the generation of false defect signals during a normal product scan, thereby limiting the sensitivity of the emulsion fault circuitry. This problem is eliminated by the transverse defect (including, specifically, roll mark defect) detector 200 of this invention, now described.

Referring to FIG. 4, the roll mark detector 200 consists of three major components, namely: a precision clamping circuit 202, which samples a time-varying waveform V and averages the values of these samples to form a bias necessary to hold signal V about a zero volt baseline value; a bipolar discriminator 210; and an AND gate 212. The elements of precision clamping circuit 202 include a sampled time averager 204 and differencer 205. An understanding of the functions of the transverse defect detector circuitry is facilitated by reference to waveforms depicted in FIGS. 3, 4A and 5A.

The difference time integrated signal V from the emulsion fault detector 30 is a simultaneous input to sampled time averager circuit 204 and differencer 205. Since waveform V is generated as a result of time integrating the difference between the product gated Q portion of the log-processed signal S and its time average U, subtle variations in the pedestal level of time sequential electrical signal A signifying a roll mark, shown in this case as an amplitude increase of the center non-flat pedestal 216, FIG. 5A, produce a significant change in the final integrated value at point 217 of the corresponding signal in waveform V. Particularly significant is that (see waveform A), due to product pedestal non-flatness, the maximum amplitudes of the three traces of waveform V vary only slightly and thus remain beyond the detection limits of emulsion fault detector 30. Interrogate pulse ZZ, originating in the digital logic and gating circuit 44, occurs in the interval between the end of the product gate Q and the emulsion fault detector difference tim integrator reset signal G and is used to trigger sampled time averager circuit 204 to sample and average over several scans the distinctive terminal value of each scan in waveform V to produce waveform BB, which is then used to form the clamp bias in differencer circuit 205.

The clamped signal output waveform RR (FIG. 5A) produced by differencer circuit 205 passes through bipolar discriminator 210, which has thresholds set according to the threshold level set voltage divider 224

(FIG. 5). Those portions of waveform RR which exceed the pre-established threshold values, e.g., shaded area 218, will cause the bipolar discriminator circuit 210 to produce the logic signal shown in waveform SS. It is apparent from examination of the adjacent pulses in waveform RR that non-flat pedestals may cause excursions of portions of these pulses beyond the threshold values set, even when a transverse (or roll mark) defect is not present. To avoid this ambiguity, AND gate 212 operates to pass only that portion of bipolar discriminator 210 output which coincides in time with interrogate signal ZZ at the end of each produt scan, to thereby produce transverse (or roll mark) defect signal FF.

It will be understood that, should a constant, small offset voltage, not related to the product scan, be present at the input of the difference time integrator 96, a zero value difference input signal to this circuit will yield a non-zero integrated output waveform V. In this event, if sufficiently large, signal V would then exceed the emulsion fault thresholds 100 and trigger the emulsion fault alarm 109. However, the transverse (or roll mark) defect detector will not then be affected, since the change in clamping level BB offsets the increase in waveform V amplitude, so that signal RR remains within the pre-established transverse (or roll mark) defect discriminator threshold levels.

FIG. 5 shows, in schematic diagram, a preferred embodiment of the transverse (or roll mark) defect detector circuitry. The elements which comprise the precision clamping circuit 202 are shown as two individual broken line sub-assemblies, i.e., sampled time averager 204 and differencer 205, to more clearly identify their separate functions. Precision clamping circuit 202, hereinbefore mentioned, performs a multipurpose function. Difference time integrator output signal V proceeds along two parallel paths to a unity gain differencing amplifier 215. Operational amplifier 215 can typically be a Type 141410 marketed by the Philbrick Division, Teledyne, Inc. The first path to the amplifier 215 output through 10K resistors 213 and 214 is highly responsive to the signal V. The second path through resistor 220 and FET switch 223 (typically a type CAG-10, marketed by Crystalonics Division, Teledyne, Inc.) to the non-inverting terminal of amplifier 215 is much less responsive to signal V due to the time averaging produced by the combined values of 10K resistors 220 and 221 and the 1.0 μf capacitor 222. When FET switch 223 is closed, capacitor 222 samples the signal V through resistor divider 220 and 221, and charges to a value equal to ½ V. As mentioned earlier, the signal V at, and during, each time FET switch 223 is closed is substantially constant. The effective averaging of ½ V from one switch closure to the next is directly proportional to the values of resistors 220 and 221 and capacitor 222, but inversely proportional to the fraction of time the switch (typically, a 1% duty cycle, 5 μ sec. closed period) is closed. When the FET switch opens, the average, ½ V, is maintained at the noninverting (+) amplifier 215 input by capacitor 222.

Due to the high gain characteristics of amplifier 215, and by virtue of feedback resistor 214, the inverting input of amplifier 215 is maintained at the same potential as the non-inverting input. Also, since resistors 213 and 214 have equal values, the difference between the input voltage V and output RR is equally divided across these resistors and appears at the inverting (−) input. Since the non-inverting input is maintained at ½ $V_{AVE}$, the output RR must equal $-(V-V_{AVE})$, an inverted, zero-based transverse (or roll mark) defect signal.

The ability of this circuit to precisely clamp a signal to a zero baseline value is best illustrated by using an example. Referring again to FIG. 5, suppose signal V has a constant DC value of +2.0 volts and that FET switch 223 is closed. Resistors 220 and 221 form a simple voltage divider, since capacitor 222 appears as an open circuit. Consequently, a +1.0 volt DC signal appears at the non-inverting (+) terminal of amplifier 215. By virtue of feedback, an identical +1.0 volt signal appears at the inverting (−) terminal of the amplifier. Resistors 213 and 214 also form a voltage divider between the amplifier output (RR) and the input of 2.0 volts. Because the voltage difference across resistor 213 is 1 volt and the current thus produced passes entirely through an equal resistance 214, an equal 1 volt difference occurs across 214. Thus, the output RR is zero volts for input V equal to 2.0 volts.

The residual signal RR, non-zero volt based, passes next to parallel-connected comparators 232 and 233 (typically, Type AD351K marketed by Analog Devices, Inc.) which are biased appropriately by resistors 230, 231 and 225 to serve as a bipolar discriminator 210 using (+) and (−) thresholds set by transverse (or roll mark) defect level set 224 potentiometer 224a. OR gate 211 passes defect signals of either polarity, but AND gate 212 allows only those defect signals which exceed the preset thresholds 224 at the time of the interrogate pulse ZZ to be registered as transverse (or roll mark) defects.

Referring to FIGS. 1 and 5A particularly, the operation of the complete inspection system in detecting typical transverse (or roll mark) defects is summarized as follows.

A laser-optical system 20 is used to produce a flying spot scan 21 across an optical AUTOCAL filter 23 of specified radiation attenuation characteristics and thence across a product web 22 moving in the direction indicated. The PM tube 33 produces a sequential waveform A from the energy transmitted through the product web (refer FIG. 1) and conveyed to it via radiation-conducting rod collector 32. An independent solar cell end-of-scan detector 34 produces a signal B which is a measure of the inspection beam power and initiates formation of reset pulse G produced by the digital logic and gating circuit 44.

Operation of the preamplifier and AGC circuit 43 produces an inverted, but amplified, sequential waveform C (FIG. 3) which contains the AUTOCAL and the pedestal information necessary for discriminating the wide variety of defects hereinbefore described with respect to the sharp edge defect, diffuse edge defect and emulsion fault (protracted duration defect) detections.

As described in said Application Ser. No. 383,289, the operation of the sharp edge defect detector 24 and associated alarm and product rejection apparatus 64 depend upon the results of differentiating sequential waveform C in order to detect defects which are usually quite small and have sharp edges.

Since a diffuse edge defect does not produce a sufficiently strong differentiated signal response, because the more diffuse edge conditions produce a sloping rather than sharply rising signal, it will not be detected by sharp edge defect detector 24. Therefore, to extract the diffuse edge defect information from sequential waveform C, the diffuse edge defect processor 25 uses the diffuse edge defect AUTOCAL gate N produced by the digital logic and gating circuit 44 to sample the amplitude of the AUTOCAL counterpart of pulse 45, waveform A, to establish an AUTOCAL voltage reference level. As hereinbefore described, this reference signal, A(t), is log ratioed with the product pedestal portion of sequential signal C, which has been gated by product gate Q, formed by the digital logic and gating circuit 44. The calibrated log ratioed signal output S is introduced to the diffuse edge defect detector 26 through high pass filtering and the remaining a-c component is discriminated. The occurrence of diffuse edge defect signals triggers alarm 92 and product rejection effectuation as hereinbefore described for the sharp edge defect detection system.

To extract the emulsion fault information from the calibrated log ratioed signal output S, emulsion fault detector 30 integrates the difference between the product pedestal portion of the signal S, which is gated by product gate Q, and its time-average value U. Reset signal G terminates the accumulation of the difference signals, V. Should the accumulated value, during each scan, exceed the preselected thresholds, an emulsion fault signal Y is generated which, in turn, causes the digital logic and gating circuit 44 to send out the emulsion fault hold signal X and trigger alarms 109 and product rejection action as hereinbefore described for the sharp edge and diffuse edge defect cases. This signal halts further time-averaging and replaces the time-averaged signal output with a "good product" reference XX developed in the emulsion fault hold circuitry 31. The "good product" reference level XX constitutes the last-known, best-calibrated, time-averaged signal prior to the defect-containing scan. The emulsion fault hold X and "good product" reference XX signals remain until the emulsion fault condition 93a (FIG. 4A) no longer exists, whereupon the digital logic and gating circuit 44 clears the emulsion fault hold signal X, thereby restoring the time-averaging of signal S.

Finally, to detect the subtle transverse (or roll mark) defect signal in a product scan obscured by a non-flat pedestal condition, a transverse defect detector 200 receives interrogate pulse ZZ from the digital logic and gating circuit 44, which is used to sample the terminal value of the time-integrated difference signal V for that scan (FIG. 5A) produced in the emulsion fault detector 30. The several scan (typically, about 200 scans corresponding to about 10 inches web advance) average value BB of these time sampled values establishes the zero volt clamping level needed to produce a good product reference for setting the transverse (or roll mark) defect threshold values. Those values of difference signal V which exceed the pre-established threshold values, e.g., 218 shown in waveform RR (FIG. 5A), produce defect rejection signals SS. However, only those defect signals which exist at the interrogation times ZZ are registered as transverse (or roll mark) defect signals FF. The occurrence of a transverse (or roll mark) defect thereupon activates an alarm 201 and product rejection effectuation as hereinbefore described for the preceding defect classes.

We claim:

1. In a flying spot inspection system for web materials having a radiation source, means traversing a beam of radiation from said source in a scan across said web, electronic means responsive to said beam of radiation in either the reflection mode or the transmission mode with respect to said web detecting the existence of transverse defects or defects oriented in the scan direction, discriminating means responsive to said electronic means detecting said defects identifying web materials containing said defects and passing the remainder of said web materials as acceptable product, and automatic calibration means providing at the outset of each said scan said electronic means with an instantaneous basic reference voltage signal retained during the balance of each said scan determined by operation of said system with a preselected radiation attenuation filter replacing said web at the outset of said scan, the improvement wherein said electronic means for the detection and discrimination of said transverse defects comprises:

means integrating and holding the terminal value of the integrated difference signal between each instantaneous calibrated gated pedestal signal and its time-averaged value over many scans, means sampling said held integral value at the end of each scan, means obtaining a short-term time average of the samples of said held integral values, means comparing said short-term time average of said sampled integral values with said integrated difference signal, and discriminating means evaluating the magnitude of the difference between said short-term time average of said sampled integral values and said integrated difference signals with respect to preselected (+) and (−) polarity thresholds and means to initiate an alarm for each signal exceeding said preselected thresholds at the sampling instant.

2. A flying spot inspection system for web materials according to claim 1 wherein said electronic means for the detection and discrimination of said transverse defects comprises:

a precision clamping circuit for effecting the operation (a) of sampling, holding and time averaging said terminal values of the integrated difference signal between the instantaneous calibrated gated pedestal signal and its time-averaged value over many scans and the operation (b) of differencing said integrated difference signal over a given scan with the results of the operation (a), a bipolar discriminator evaluating the magnitude of said difference between said (a) and (b) with respect to preselected (+) and (−) polarity thresholds, and an AND gate to initiate an alarm for each said difference exceeding said preselected thresholds at said sampling instant.

* * * * *